(12) United States Patent
Isaacson et al.

(10) Patent No.: US 11,701,460 B2
(45) Date of Patent: Jul. 18, 2023

(54) OCCLUSION DETECTION DEVICES, SYSTEMS, AND METHODS

(71) Applicant: Becton, Dickinson and Company, Franklin Lakes, NJ (US)

(72) Inventors: S. Ray Isaacson, Layton, UT (US); Vincent J. Sullivan, Cary, NC (US); Brendan Tompkins, Cary, NC (US); Charles D. Shermer, Raleigh, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 88 days.

(21) Appl. No.: 16/841,398

(22) Filed: Apr. 6, 2020

(65) Prior Publication Data
US 2020/0316292 A1 Oct. 8, 2020

Related U.S. Application Data

(60) Provisional application No. 62/830,707, filed on Apr. 8, 2019.

(51) Int. Cl.
| | |
|---|---|
| *A61M 5/168* | (2006.01) |
| *A61M 39/10* | (2006.01) |
| *G16H 20/17* | (2018.01) |
| *A61M 1/36* | (2006.01) |
| *A61M 1/00* | (2006.01) |

(52) U.S. Cl.
CPC ............ *A61M 1/3656* (2014.02); *A61M 1/73* (2021.05); *A61M 1/74* (2021.05); *A61M 1/86* (2021.05); *A61M 5/16831* (2013.01); *A61M 39/10* (2013.01); *G16H 20/17* (2018.01); *A61M 1/734* (2021.05); *A61M 2005/16863* (2013.01); *A61M 2205/18* (2013.01); *A61M 2205/3334* (2013.01); *A61M 2205/3553* (2013.01); *A61M 2205/50* (2013.01)

(58) Field of Classification Search
CPC .......... A61M 5/16831; A61M 5/16854; A61M 2005/16863; A61M 2005/16868; A61M 2005/16872; A61M 5/16886; A61M 1/3656
See application file for complete search history.

(56) References Cited

U.S. PATENT DOCUMENTS

| | | | | |
|---|---|---|---|---|
| 4,195,515 | A * | 4/1980 | Smoll | G01F 15/18 73/861.15 |
| 5,533,412 | A | 7/1996 | Jerman et al. | |
| 6,283,719 | B1 * | 9/2001 | Frantz | F04B 43/00 417/53 |
| 6,482,185 | B1 * | 11/2002 | Hartmann | A61M 5/31525 604/211 |
| 2009/0157040 | A1 | 6/2009 | Jacobson et al. | |
| 2011/0319728 | A1 | 12/2011 | Petisce et al. | |

(Continued)

*Primary Examiner* — Amber R Stiles
*Assistant Examiner* — Leah J Swanson
(74) *Attorney, Agent, or Firm* — Kirton McConkie; Whitney Blair; Kevin Stinger

(57) ABSTRACT

A monitoring device may include a housing, which may include a distal end, a proximal end, and a fluid pathway extending through the proximal end and distal end. The distal end may include a connector configured to couple to a catheter assembly. The monitoring device may include one or more sensors disposed within the fluid pathway. The sensors may facilitate identification of an occlusion within the catheter assembly.

14 Claims, 8 Drawing Sheets

(56) References Cited

U.S. PATENT DOCUMENTS

2012/0029333 A1\* 2/2012 Dogwiler .............. A61M 5/158
  600/365
2015/0283309 A1 10/2015 Look et al.
2017/0266399 A1\* 9/2017 Campana ............ A61M 16/107
2018/0214634 A1\* 8/2018 Neftel ............... A61M 5/16854

\* cited by examiner

OCCLUSION DETECTION DEVICES, SYSTEMS, AND METHODS

RELATED APPLICATIONS

This application claims the benefit of U.S. Application No. 62/830,707, filed Apr. 8, 2019, and entitled OCCLUSION DETECTION DEVICES, SYSTEMS, AND METHODS, which is incorporated herein in its entirety.

BACKGROUND

Infusion therapy, a common healthcare procedure, may be facilitated by a vascular access device. Hospitalized, home care, and other patients often receive fluids, pharmaceuticals, and blood products via the vascular access device. Blood withdrawal is another common healthcare procedure that may be facilitated by the vascular access device.

The vascular access device may insert a peripheral and/or central vasculature of a patient. The vascular access device may be indwelling for short term (days), moderate term (weeks), or long term (months to years). The vascular access device may be used for continuous infusion therapy or for intermittent infusion therapy. A common type of vascular access device is a catheter, such as, for example, a peripheral intravenous catheter (PIVC) or a peripherally inserted central catheter (PICC).

When the catheter remains in the vasculature of the patient for a prolonged period of time, the catheter may become more susceptible to an occlusion or blockage by debris (e.g., fibrin or platelet clots). The occlusion can lead to catheter infection, pulmonary embolism, post-thrombotic syndrome, and other negative health outcomes. Also, when the occlusion in the catheter occurs, the catheter may be removed and/or replaced, which may result in an additional needle stick, pain to the patient, and higher material costs.

Currently clinicians are left to their own judgment to assess whether or not the catheter is occluded. The clinician may judge whether the catheter is partially or fully occluded based on difficulty in getting blood return or by syringe pressure. Clinicians may not be well equipped to judge whether the catheter is nearing full occlusion. In response to making a judgment that the catheter is partially or fully occluded, the clinician may intervene to clear the occlusion.

Current occlusion removal or prevention measures include manually flushing the catheter. Also, a thrombolytic agent may be used to break up the occlusion in the catheter. However, the thrombolytic agent is often expensive and installation of the thrombolytic agent may interrupt infusion therapy through the catheter.

The subject matter claimed herein is not limited to embodiments that solve any disadvantages or that operate only in environments such as those described above. Rather, this background is only provided to illustrate a technology area where some implementations described herein may be practiced.

SUMMARY

The present disclosure relates generally to a monitoring device to monitor a status of a catheter, which may be indwelling in a vasculature of a patient. In some embodiments, the catheter may include a PIVC, a PICC, or a midline catheter. In some embodiments, the monitoring device may include a housing that includes a distal end, a proximal end, and a fluid pathway extending through the proximal end of the housing and the distal end of the housing.

In some embodiments, the distal end of the housing may include a connector configured to couple to a catheter assembly, which may include the catheter. In some embodiments, the distal end of the housing may include another connector. In some embodiments, the distal end of the housing and/or the proximal end of the housing may include a luer connector.

In some embodiments, the monitoring device may include one or more sensors disposed within the fluid pathway. In some embodiments, the monitoring device may include a communication unit configured to wirelessly transmit an output signal to a receipt location. In some embodiments, the output signal may be based on data sensed by the sensors. In some embodiments, the housing may include one or more of the following: a printed circuit board, a power supply, and an electrical contact. In some embodiments, the communication unit and/or a processor may be disposed on the printed circuit board.

In some embodiments, the monitoring device may include another housing that may be removably coupled to the housing. In some embodiments, the other housing may include one or more of the following: the printed circuit board, the power supply, and another electrical contact. In some embodiments, the other electrical contact of the other housing may be operably connected to the electrical contact of the housing, which may facilitate communication between the sensors disposed within the housing and the printed circuit board within the other housing.

In some embodiments, at least one of the sensors disposed within the fluid pathway may include a pressure sensor, which may be configured to detect a fluid pressure of fluid within the fluid pathway. In some embodiments, at least one of the sensors may include a flow sensor, which may be configured to detect a fluid flow rate and/or a fluid flow volume within the fluid pathway. In some embodiments, the monitoring device may include another pressure sensor that may be placed proximal to the pressure sensor.

In some embodiments, the printed circuit board may include the processor. In some embodiments, presence of an occlusion in the catheter assembly may be determined based on the data sensed by the sensors. In some embodiments, the occlusion may be partial, partially blocking fluid flow through the catheter assembly, or full, fully or substantially fully blocking fluid flow through the catheter assembly. In some embodiments, in response to determining the presence of the occlusion based on the data sensed by the sensor and/or the other sensor, the communication module may wirelessly transmit the output signal to the receipt location.

In some embodiments, in response to receipt of the output signal by the receipt location, an alert may be provided at the receipt location. In some embodiments, the alert may include a sound, a tactile vibration, or a visual cue, such as, for example, a change in status of a light. In some embodiments, an indicator at the receipt location may be configured to provide the alert. Additionally or alternatively, in some embodiments, an indicator on the housing and/or the other housing may be configured to provide the alert in response to the determining the presence of the occlusion.

In some embodiments, the monitoring device may transmit the output signal to the receipt location via a network. In some embodiments, the receipt location may include a patient electronic medical record, a storage device, a smartphone or another mobile device, a computer server, a barcode scanner, a laptop computer, a nurse station, a printer, or another suitable receipt location.

In some embodiments, a method of determining the presence of the occlusion in the catheter assembly may include coupling the monitoring device to the catheter assembly, which may be indwelling. In some embodiments, the method may include determining the presence of the occlusion within the catheter assembly based on the data sensed by the sensors. In some embodiments, the method may include transmitting the output signal from the communications module to the receipt location in response to determining the presence of the occlusion within the catheter assembly.

In some embodiments, determining the presence of the occlusion within the catheter assembly based on the data sensed by the sensors may include determining the occlusion is partial in response to the sensors detecting a mean maximum pressure between 14 psi and 42.5 psi within the fluid pathway. In some embodiments, the method may include providing the alert in response to determining the occlusion is partial. In some embodiments, determining the presence of the occlusion within the catheter assembly based on the data sensed by the sensors may include determining the occlusion is full in response to the sensors detecting a mean maximum pressure of at least 42.5 psi. In some embodiments, the method may include providing the alert in response to determining the occlusion is full.

In some embodiments, determining the presence of the occlusion within the catheter assembly based on the data sensed by the sensors may include determining a pressure, such as the mean maximum pressure, within the catheter assembly is greater than a threshold value. In some embodiments, the sensors may include a first pressure sensor and a second pressure sensor, which may be disposed proximal to the first pressure sensor within the fluid pathway. In some embodiments, the method may include determining a fluid flow direction within the catheter assembly based on the data sensed by the first pressure sensor and the second pressure sensor.

In some embodiments, the sensors may include a first flow sensor and a second flow sensor, which may be disposed proximal to the first flow sensor within the fluid pathway. In some embodiments, the method may include determining a fluid flow direction within the catheter assembly based on the data sensed by the first flow sensor and the second flow sensor.

It is to be understood that both the foregoing general description and the following detailed description are examples and explanatory and are not restrictive. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present disclosure. The following detailed description is, therefore, not to be taken in a limiting sense.

BRIEF DESCRIPTION OF SEVERAL VIEWS OF THE DRAWINGS

Example embodiments of the invention will be described and explained with additional specificity and detail through the use of the accompanying drawings in which.

DESCRIPTION OF EMBODIMENTS

Figure 1A:
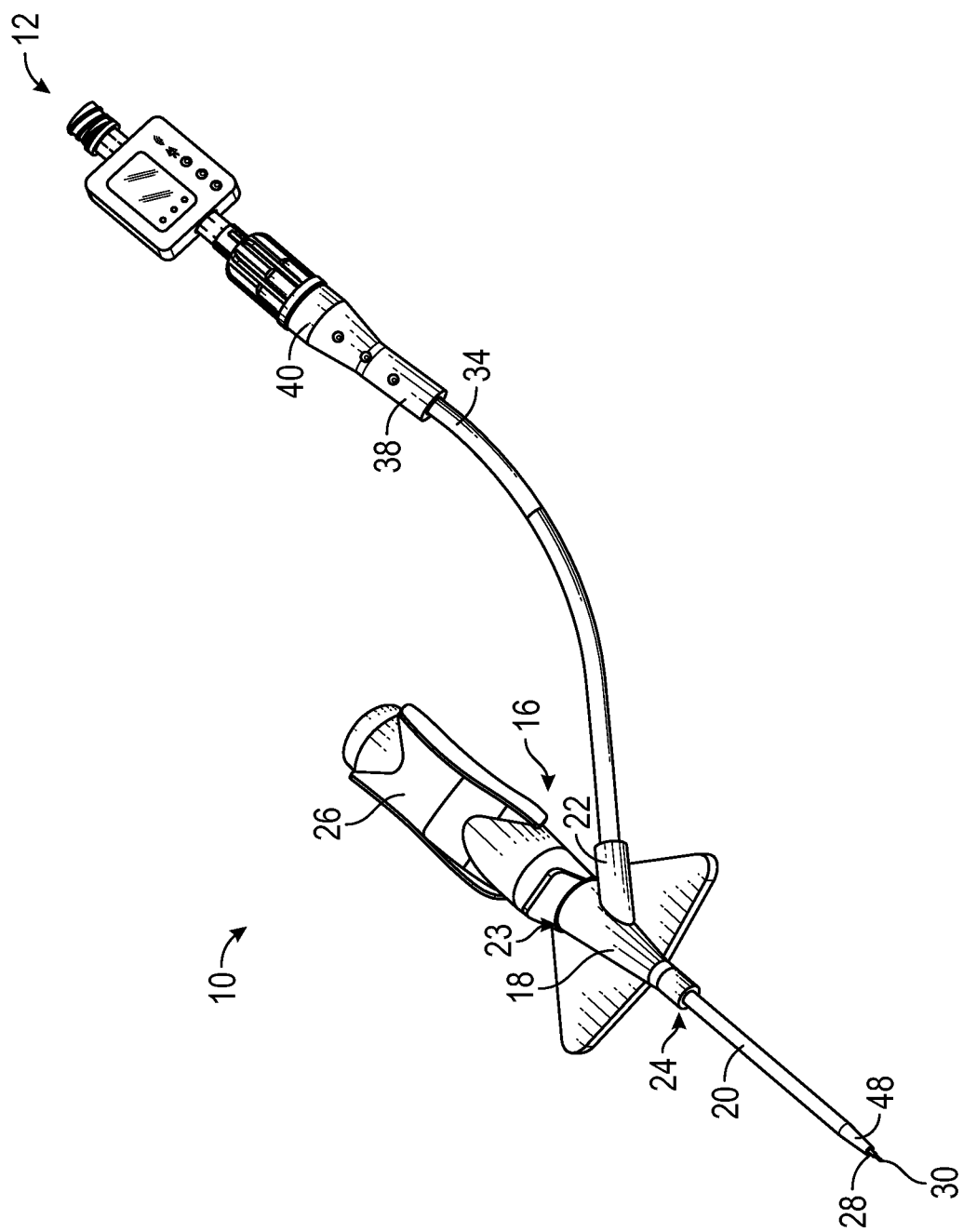
FIG. 1A is an upper perspective view of an example monitoring device coupled to an example catheter assembly, according to some embodiments.

Referring now to FIG. 1A, an example catheter system 10 is illustrated, according to some embodiments. In some embodiments, the catheter system 10 may include a monitoring device 12 and a catheter assembly 16, which may be coupled to the monitoring device 12.

In some embodiments, the catheter assembly 16 may include a catheter adapter 18 and a catheter 20 extending distally from the catheter adapter 18. In some embodiments, the catheter adapter 18 may include a side port 22 in fluid communication with the lumen of the catheter adapter 18. In some embodiments, the catheter adapter 18 may include a proximal end 23, a distal end 24, and a lumen extending there between. In some embodiments, the catheter 20 may include a PIVC, a PICC, or a midline catheter.

In some embodiments, the catheter assembly 16 may be removably coupled to a needle assembly, which may include a needle hub 26 and an introducer needle 28. In some embodiments, the introducer needle 28 may include a sharp distal tip 30. In some embodiments, a proximal end of the introducer needle 28 may be secured within the needle hub 26. In some embodiments, the introducer needle 28 may extend through the catheter 20 when the catheter assembly 16 is in an insertion position ready for insertion into vasculature of a patient, as illustrated, for example, in FIG. 1A. In some embodiments, in response to the introducer needle 28 being inserted into the vasculature of the patient, blood flashback may flow through the sharp distal tip 30 of the introducer needle 28 and may be visible to a clinician between the introducer needle 28 and the catheter 20 and/or at another location within the catheter assembly 16.

In some embodiments, in response to confirmation via the blood flashback that the catheter 20 is positioned within vasculature of the patient, the needle assembly may be removed from the catheter assembly 16. In some embodiments, when the needle assembly is coupled to the catheter assembly 16, as illustrated, for example, in FIG. 1A, the introducer needle 28 of the needle assembly may extend through a septum disposed within the lumen of the catheter adapter 18.

In some embodiments, the catheter assembly 16 may include an extension tube 34. In some embodiments, a distal end of the extension tube 34 may be integrated with the catheter adapter 18, as illustrated, for example, in FIG. 1A. For example, the extension tube 34 may be integrated with the side port 22 of the catheter adapter 18. In some embodiments, the extension tube 34 may be removably coupled to the catheter adapter 18.

In some embodiments, an adapter 38 may be coupled to a proximal end of the extension tube 34. In some embodiments, the adapter 38 may include a Y-adapter or another suitable connector. In some embodiments, a needleless connector 40 may be coupled to the adapter 38. In some embodiments, the adapter 38 and/or the needleless connector 40 may be used to couple the catheter 20 with the monitoring device 12. In some embodiments, a medical device for fluid administration or blood withdrawal may be coupled to a proximal end of the monitoring device 12. The medical device may include a transfusion bag, syringe, or any other suitable medical device.

Figure 1B:
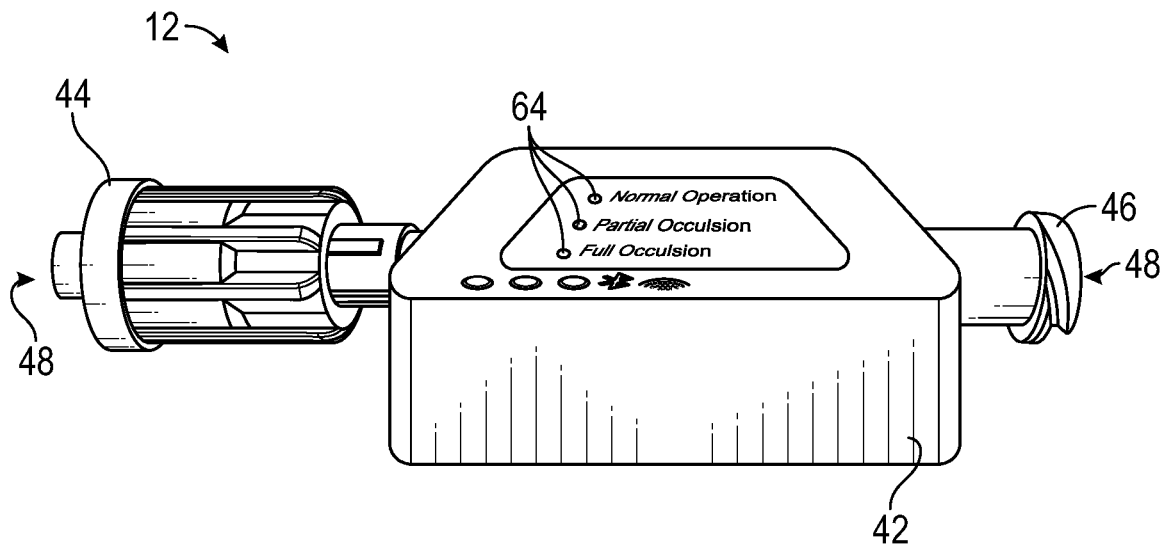
FIG. 1B is an upper perspective view of the monitoring device of FIG. 1A, according to some embodiments.

Referring now to FIG. 1B, in some embodiments, the monitoring device 12 may include a housing 42, which may include a distal end 44, a proximal end 46, and a fluid pathway 48 extending through the proximal end 46 and the distal end 44. In some embodiments, the distal end 44 may include a connector configured to couple to the catheter assembly 16. In some embodiments, the proximal end 46 may include another connector. In some embodiments, the connector and/or the other connector may include a male or female Luer connector. In some embodiments, the Luer connector may include a Luer-slip or a Luer-lock feature.

Referring now to FIG. 2A-2E, in some embodiments, the monitoring device 12 may include one or more sensors within the fluid pathway 48. In some embodiments, the fluid pathway 48 may be in fluid communication with a fluid pathway extending through the catheter assembly 16. Thus, by detecting conditions within the fluid pathway 48, the sensors may detect conditions within the fluid pathway extending through the catheter assembly 16.

Figure 2A:
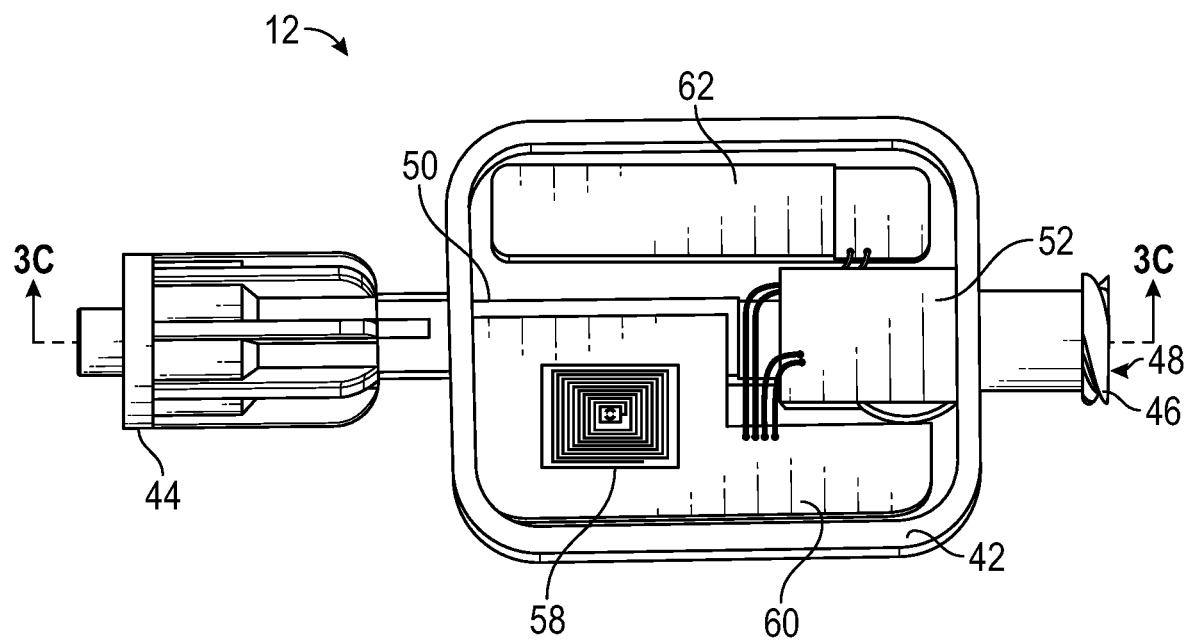
FIG. 2A is a partial cutaway view of the monitoring device of FIG. 1A, according to some embodiments.
Figure 2B:
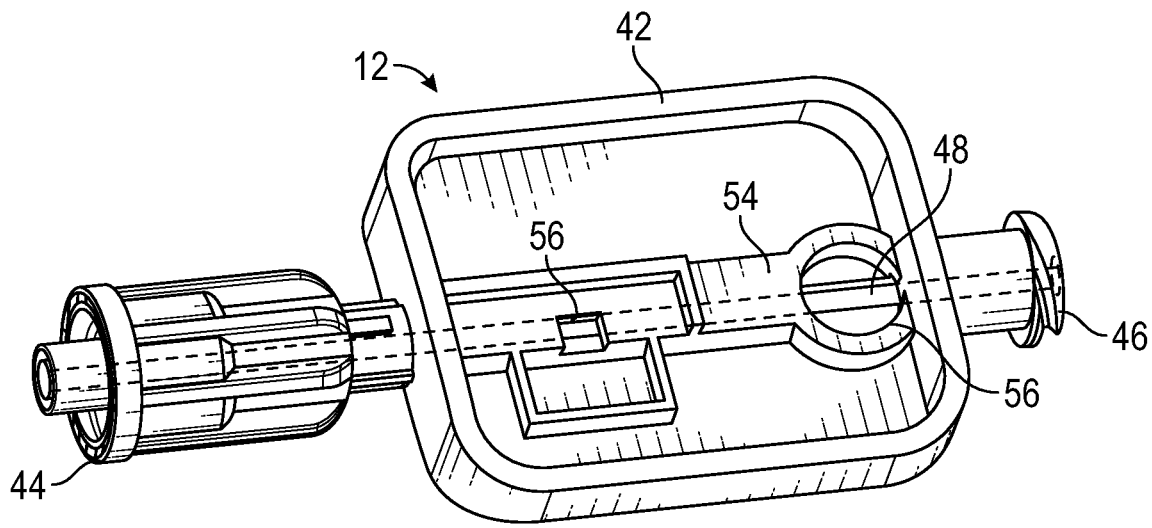
FIG. 2B is another partial cutaway view of the monitoring device of FIG. 1A, illustrating an example circuit board, example battery, and example sensors removed, according to some embodiments.
Figure 2C:
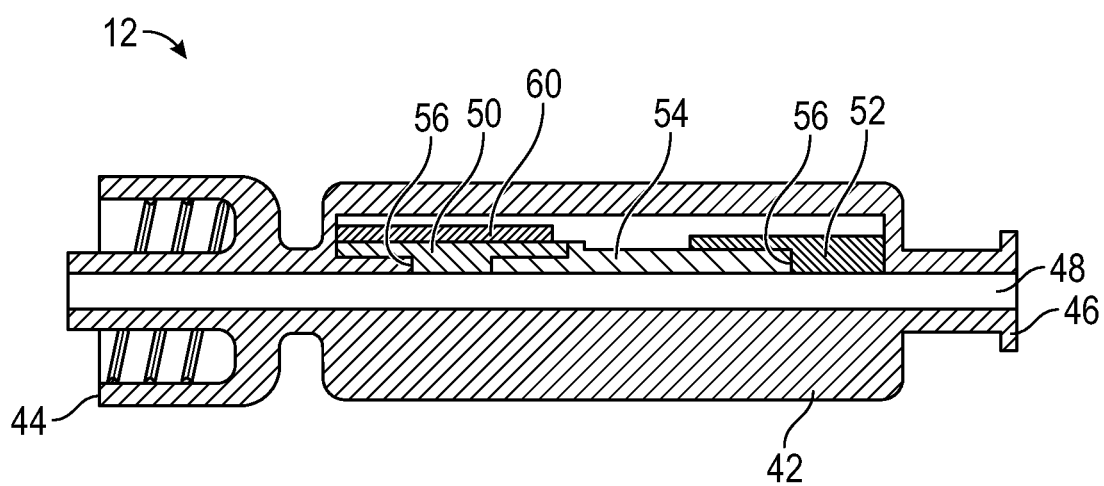
FIG. 2C is a cross-sectional view of the monitoring device of FIG. 1A along the line 2C-2C of FIG. 2A, according to some embodiments.

As illustrated, for example, in FIG. 2A-2C, in some embodiments, the sensors may include a flow sensor 50 and/or a pressure sensor 52. In some embodiments, the flow sensor 50 may be disposed distal to the pressure sensor 52. In some embodiments, the flow sensor 50 may be disposed proximal to the pressure sensor 52. For example, a position of the flow sensor 50 and the pressure sensor 52 may be reversed from that illustrated in FIG. 2A. In some embodiments, the sensors may be positioned at various locations with respect to the fluid pathway 48.

In some embodiments, the flow sensor 50 may be configured to detect a fluid flow rate and/or a fluid flow volume within the fluid pathway 48. In some embodiments, the pressure sensor 52 may be configured to detect a fluid pressure of fluid within the fluid pathway 48. In some embodiments, the fluid pathway 48 may be enclosed within the housing 42 such that fluid may not leak out of the fluid pathway 48 as the fluid flows between the distal end 44 and the proximal end 46. In some embodiments, the fluid pathway 48 may extend through a tunnel 54, which may include one or more holes 56 through which the sensors may extend to enclose the fluid pathway 48.

In some embodiments, the flow sensor 50 may include any suitable flow sensor that may detect fluid flow through the fluid pathway 48. Various suitable fluid flow sensors are well known, and may be used. Illustrative examples of suitable fluid flow sensors may include, but are not limited to, optical sensors, piezoelectric sensors, sound sensors, reed switch-based sensors, magnetic sensors, ultrasound sensors, orifice type flow meters, venturi flow meters, and the like.

In some embodiments, the flow sensor 50 may include a thermal flow meter. In some embodiments, the thermal flow meter may include a heater, which may heat the fluid travelling through the fluid pathway 48. In some embodiments, the thermal flow meter may be configured to measure the fluid temperature at an upstream point and a downstream point within the fluid pathway 48. In some embodiments, fluid flow rate may be determined based on a temperature difference between the upstream point and the downstream point. In some embodiments, the heater may be controlled to constantly maintain a fixed temperature, and the fluid flow rate may be determined based on an amount of power necessary to maintain the fixed temperature. An example flow sensor may be described in U.S. Pat. No. 5,533,412, filed Jun. 7, 1995, entitled "PULSED THERMAL FLOW SENSOR SYSTEM," which is hereby incorporated by reference in its entirety.

In some embodiments, the pressure sensor 52 may include any suitable flow sensor that may detect fluid pressure within the fluid pathway 48. In some embodiments, the pressure sensor 52 may include a pressure sensitive device, which may be capacitive, resistive, optical, or ultrasonic. In some embodiments, a first surface of the pressure sensor 52 may be exposed to the fluid within the fluid pathway 48 and a second surface of the pressure sensor 52 (i.e., the reference surface) may be exposed to a liquid or gas at a reference pressure. In some embodiments, the measured pressure differential between the first surface and the second surface of the pressure sensor 52 may provide an indication of the fluid pressure to which the first surface is exposed.

In some embodiments, the monitoring device 12 may include a communication unit 58 configured to wirelessly transmit an output signal to a receipt location. In some embodiments, the output signal may be based on data sensed by the sensors. In some embodiments, a printed circuit board ("PCB") 60 and/or a power supply 62 may be disposed within the housing 42. In some embodiments, the power supply 62 may include a battery, which may be rechargeable and/or replaceable. In some embodiments, a location of the PCB 60 and/or the power supply 62 within the housing 42 may vary.

In some embodiments, the power supply 62 may be electrically coupled to the sensors and may be configured to power the sensors. In some embodiments, the power supply 62 may be remotely disposed from the PCB 60 and even the catheter assembly 16. In some embodiments, a non-volatile memory storage location, such as flash memory for instance, may be included on the PCB 60 to enable data sensed by the sensors to be temporarily or permanently stored thereon. In some embodiments, the storage location may be accessible by a user and/or can be transmitted to the receipt location.

In some embodiments, the communication unit 58 and/or a processor may be disposed on the PCB 60, which may be electrically coupled to the sensors. In some embodiments, presence of an occlusion in the catheter assembly 16 may be determined based on the data sensed by the sensors. In some embodiments, the occlusion may be partial, partially blocking fluid flow through the catheter assembly, or full, fully or substantially fully blocking fluid flow through the catheter assembly. In some embodiments, in response to the determining the presence of the occlusion based on the data sensed by the sensors, the communication unit 58 may wirelessly transmit the output signal to the receipt location.

In some embodiments, in response to receipt of the output signal by the receipt location, an alert may be provided at the receipt location. In some embodiments, the alert may include a sound, a tactile vibration, or a visual cue, such as, for example, a change in status of a light. In some embodiments, an indicator at the receipt location may be configured to provide the alert.

Additionally or alternatively, in some embodiments, an indicator on the housing 42 may be configured to provide the alert in response to the determining the presence of the occlusion. In some embodiments, the indicator may include one or more of lights, which may be arranged in various configurations. Referring back to FIG. 1B, in some embodiments, the alert may include a visual cue, which may include a change in status of one or more lights 64. For example, one or more of the lights 64 may turn on or change color in response to the determining the presence of the occlusion, such as a partial occlusion or a full occlusion.

Referring back to FIGS. 2A-2E, in some embodiments, presence of a gas bubble in the fluid pathway 48 may be determined in response to the pressure sensor 52 detecting a drop in fluid pressure within the fluid pathway 48. In some embodiments, a magnitude of the drop may be greater than a predetermined threshold value. In some embodiments, the indicator on the housing 42 and/or at the receipt location may be configured to provide the alert in response to the determining the presence of the gas bubble.

In some embodiments, the monitoring device 12 may transmit the output signal to the receipt location via a network. In some embodiments, the receipt location may include a patient electronic medical record, a storage device, a smartphone or another mobile device, a computer server, a barcode scanner, a laptop computer, a nurse station, a printer, or another suitable receipt location.

Figure 2D:
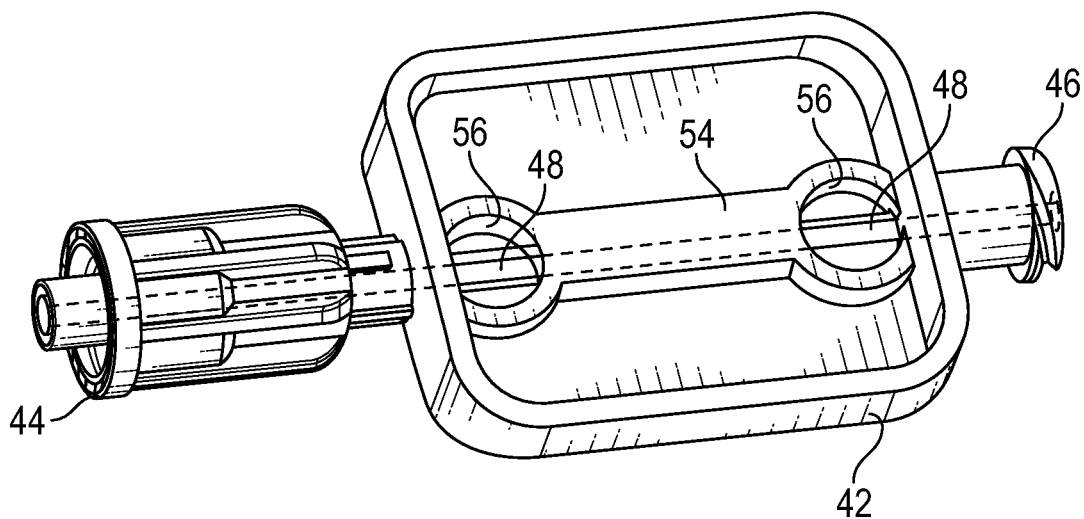
FIG. 2D is another partial cutaway view of the monitoring device of FIG. 1A, according to some embodiments.

In some embodiments, as illustrated, for example, in FIG. 2D, the sensors may include at least two pressure sensors, which may include or correspond to the pressure sensor 52 of FIG. 2A. In some embodiments, the two pressure sensors may provide a more robust determination of an occlusion within the catheter system 10 and/or may facilitate determination of fluid flow direction within the fluid pathway 48. In some embodiments, the fluid flow direction may be determined in response to a first of the two pressure sensors detecting an increase in fluid pressure within the fluid pathway 48 prior to or after a second of the two pressure sensor.

In some embodiments, the gas bubble in the fluid pathway 48 may be determined in response to one or more of the two pressure sensors detecting a drop in fluid pressure within the fluid pathway 48. In some embodiments, a direction of travel of the gas bubble may be determined in response to the first of the two pressure sensors detecting a decrease in fluid pressure within the fluid pathway 48 prior to or after the second of the two pressure sensors.

Figure 2E:
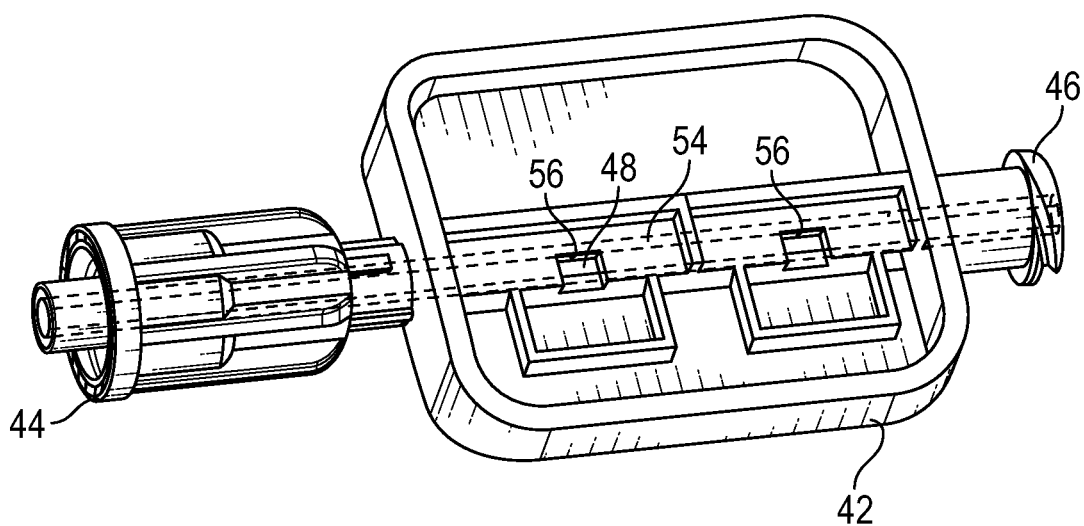
FIG. 2E is another partial cutaway view of the monitoring device of FIG. 1A, according to some embodiments.

In some embodiments, as illustrated, for example, in FIG. 2E, the sensors may include at least two flow sensors, which may include or correspond to the flow sensor 50 of FIG. 2A. In some embodiments, the fluid flow direction may be determined in response to a first of the two flow sensors detecting an increase in fluid pressure within the fluid pathway 48 prior to or after a second of the two flow sensors.

Figure 3A:
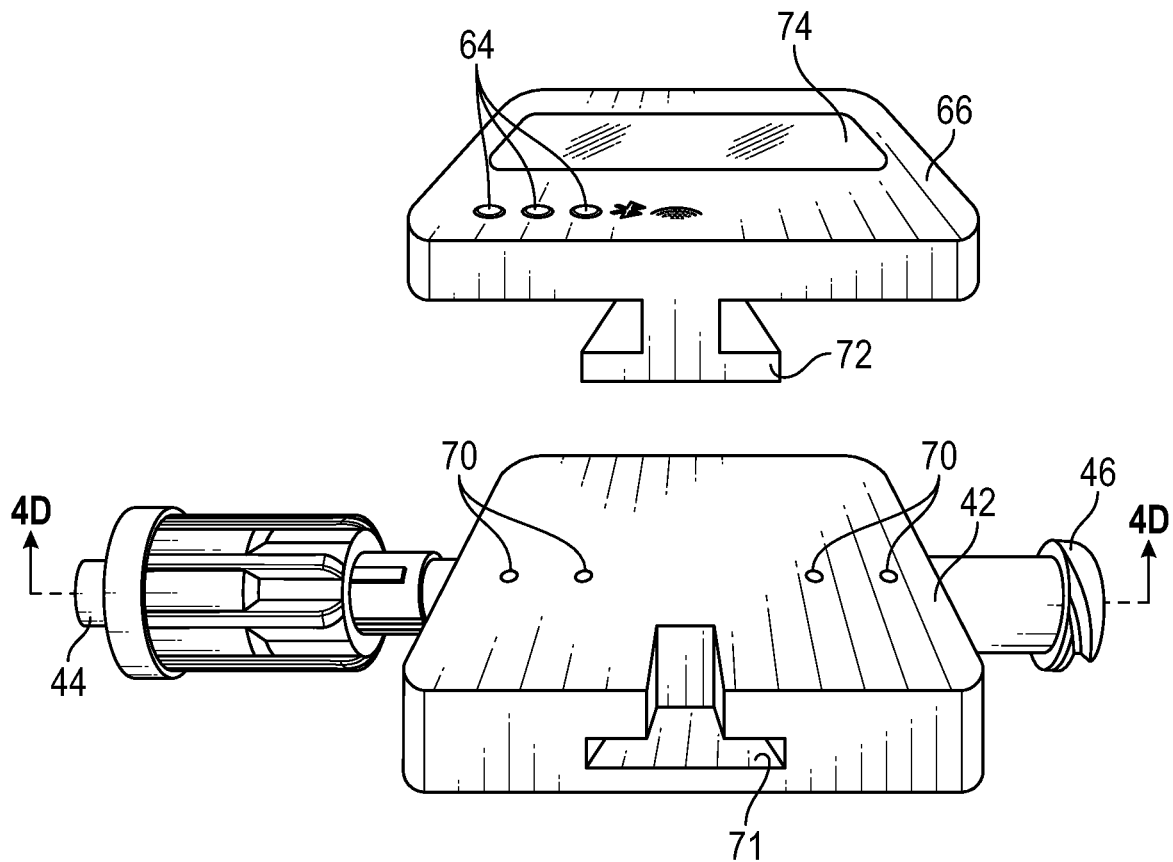
FIG. 3A is an exploded view of another example monitoring device, according to some embodiments.
Figure 3B:
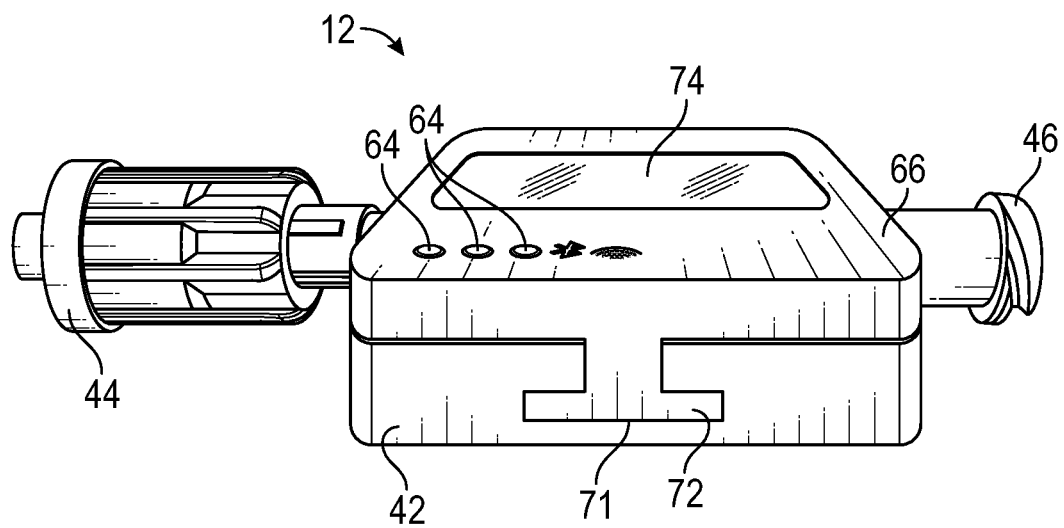
FIG. 3B is an upper perspective view of the monitoring device of FIG. 3A, according to some embodiments.
Figure 3C:
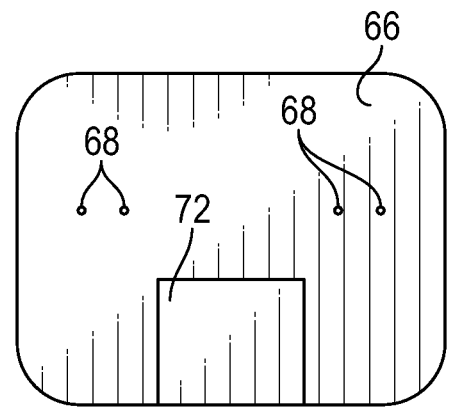
FIG. 3C is a bottom view of a first housing of the monitoring device of FIG. 3A, according to some embodiments.
Figure 3D:
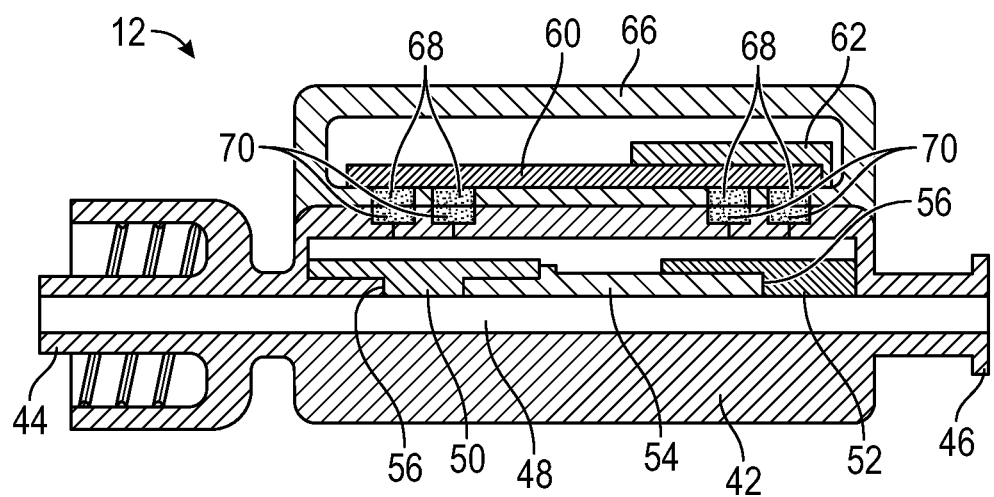
FIG. 3D is a side view of the monitoring device of FIG. 3A, according to some embodiments.

Referring now to FIG. 3A-3D, in some embodiments, another housing 66 may be removably coupled to the housing 42. In some embodiments, the other housing 66 may include one or more of the following: the PCB 60, the power supply 62, and one or more electrical contacts 68. In some embodiments, the housing 42 may include one or more other electrical contacts 70, which may be operably coupled to the electrical contacts 68 of the other housing 66 such that the power supply 62 may provide power to the sensors and/or data from the sensors may be transmitted to the PCB 60. As illustrated in FIG. 3D, the other electrical contacts 70 may be embedded in a planar top surface of the housing 42, and the electrical contacts 68 may be embedded in a planar bottom surface of the other housing 66.

In some embodiments, the housing 42 and the other housing 66 may be coupled together via any suitable coupling mechanism, including, for example, threading, a snap fit, an interference fit, friction, or an adhesive. In some embodiments, the housing 42 or the other housing 66 may include a groove or cavity 71. In some embodiments, the housing 42 or the other housing 66 may include a protrusion 72, which may be configured to fit snugly within the groove or cavity 71. The protrusion 72 may have an inverted T-shape, and the groove or cavity 71 may have a corresponding inverted T-shape. The protrusion 72 and the groove or cavity 71 may be configured such that when the inverted T-shape is fully slid into the corresponding inverted T-shape, the planar bottom surface is secured against and aligned with the planar top surface, and the electrical contacts 68 align with and contact the other electrical contacts 70.

In some embodiments, the housing 42 may be disposable after use, and the other housing 66 may be reusable. In some embodiments, the other housing 66 may be cleaned and reused for care of other patients. In some embodiments, the other housing 66 may be uncoupled from the housing 42 and coupled to another housing similar to the housing 42. In some embodiments, placement of the PCB 60 and/or the communication unit 58 in the other housing 66 may provide space in the housing 42 for the sensors and/or may prevent replacement of the PCB 60, a relatively expensive component, when the housing 42 is replaced.

In some embodiments, the other housing 66 may include the indicator configured to provide the alert in response to determining the presence of the occlusion. For example, the other housing 66 may include the lights 64, which may be arranged in various configurations. In some embodiments, the lights 64 and/or descriptions proximate the lights 64 may be arranged as illustrated, for example, in FIG. 1B. In some embodiments, the lights 64 may turn on or change color in response to determining the presence of the occlusion, such as a partial occlusion or a full occlusion indicator. In some embodiments, the housing 42 and/or the other housing 66 may include a display 74, which may be the indicator.

Figure 4:
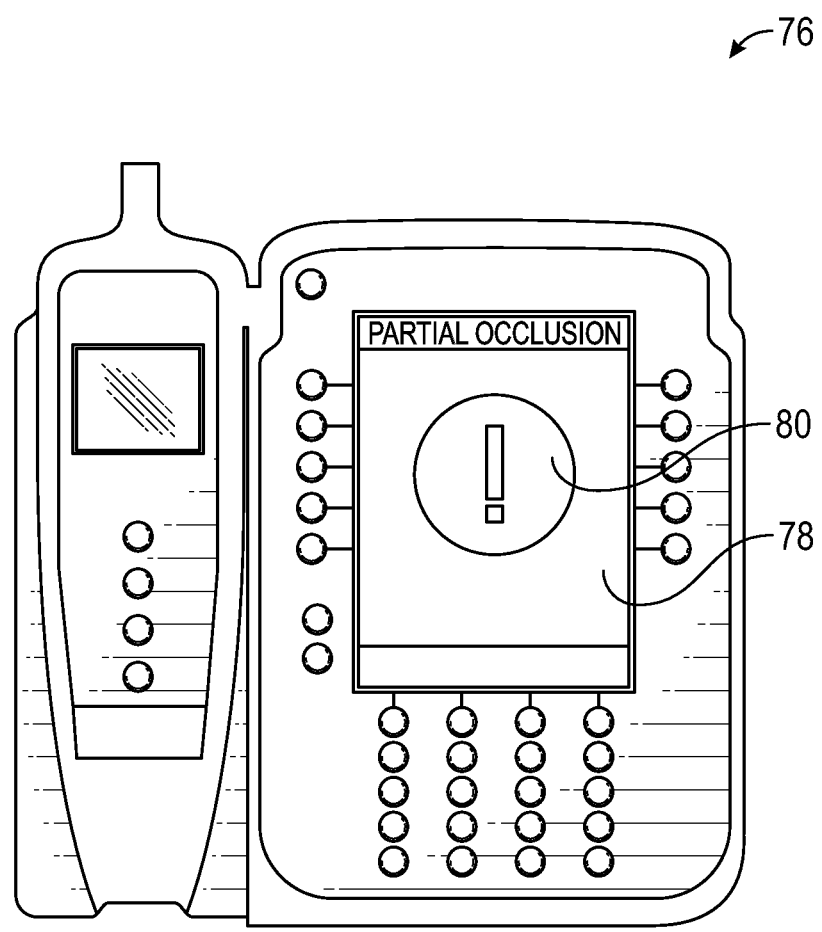
FIG. 4 is an upper perspective view of an example receipt location, according to some embodiments.

Referring now to FIG. 4, an example receipt location is illustrated, according to some embodiments. In some embodiments, the receipt location may include a clinician monitoring device 76. Examples of the clinician monitoring device 76 may include a computing device, a mobile phone, a smartphone, a tablet computer, a laptop computer, a desktop computer, a medical device, or a connected device (e.g., a smartwatch, smart glasses, or any other connected device). In some embodiments, in addition to or as an alternative to the monitoring device 12 providing the alert, the clinician monitoring device 76 may provide the alert. In some embodiments, the clinician monitoring device 76 may include a pump, which may be coupled to the proximal end 46 of the monitoring device 12 and configured to infuse the catheter system 10 in response to receipt of the output signal.

In some embodiments, the clinician monitoring device 76 may include a display screen 78, which may provide the alert. In some embodiments, the alert may include a phrase such as, for example, "Partial Occlusion" or "Full Occlusion." In some embodiments, the alert may include a visual cue on the display screen 78, such as a portion 80 of the display screen 78 that lights up or changes color. In some embodiments, the portion 80 of the display screen 78 may blink or change a rate of blinking to provide the alert. In some embodiments, an electronic health record that may be presented on the display screen 78 of the clinician monitoring device 76.

Figure 5:
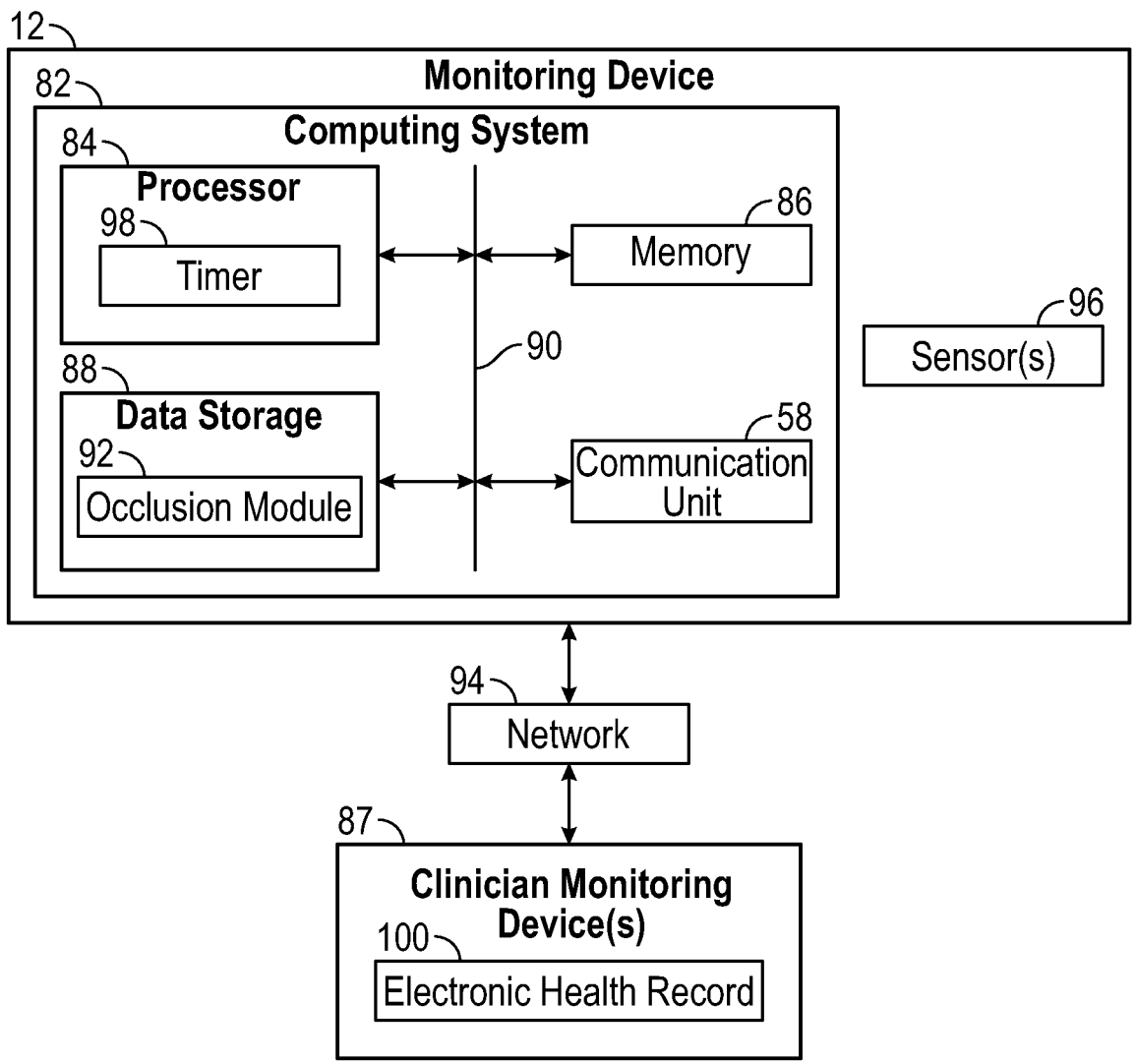
FIG. 5 is a block diagram of an example monitoring system, according to some embodiments.

FIG. 5 is as block diagram of the monitoring device 12, arranged in accordance with at least one embodiment described in the present disclosure. In some embodiments, the monitoring device 12 may include a computing system 82, which may include the PCB 60, described, for example, with respect to FIG. 2A.

In some embodiments, the computing system 82 may include a processor 84, a memory 86, a data storage 88, and a communication unit 58. In some embodiments, the processor 84, the memory 86, the data storage 88, and the communication unit 58 may be communicatively coupled by a bus 90. The bus 90 may include, but is not limited to, a controller area network (CAN) bus, a memory bus, a storage interface bus, a bus/interface controller, an interface bus, or the like or any combination thereof. In some embodiments, the processor 84 may include a timer 98. In some embodiments, the timer 98 may be a separate component linked to the processor 84.

In general, the processor 84 may include any suitable special-purpose or general-purpose computer, computing entity, or processing device including various computer hardware or software modules and may be configured to execute instructions stored on any applicable computer-readable storage media. For example, the processor 84 may include a microprocessor, a microcontroller, a digital signal processor (DSP), an application-specific integrated circuit (ASIC), a Field-Programmable Gate Array (FPGA), or any other digital or analog circuitry configured to interpret and/or to execute program instructions and/or to process data. Although illustrated as a single processor in FIG. 5, the processor 84 may include any number of processors configured to perform, individually or collectively, any number of operations described in the present disclosure. Additionally, one or more of the processors 84 may be present on one or more different electronic devices.

In some embodiments, the processor 84 may interpret and/or execute program instructions and/or process data stored in the memory 86, the data storage 88, or the memory 86 and the data storage 88. In some embodiments, the processor 84 may fetch program instructions from the data storage 88 and load the program instructions in the memory 86. In some embodiments, after the program instructions are loaded into memory 86, the processor 84 may execute the program instructions.

For example, in some embodiments, an occlusion module 92 may be included in the data storage 88 as program instructions. In some embodiments, the occlusion module 92 may be configured to manage flow conditions in a catheter system, such as, for example, the catheter system 10, described with respect to FIG. 1. The processor 84 may fetch the program instructions of the occlusion module 92 from the data storage 88 and may load the program instructions of the occlusion module 92 in the memory 86. After the program instructions of the occlusion module 92 are loaded into the memory 86, the processor 84 may execute the program instructions such that the computing system 82 may implement the operations associated with the occlusion module 92 as directed by the instructions.

The memory 86 and the data storage 88 may include computer-readable storage media for carrying or having computer-executable instructions or data structures stored thereon. Such computer-readable storage media may include any available media that may be accessed by a general-purpose or special-purpose computer, such as the processor 84. By way of example, and not limitation, such computer-readable storage media may include tangible or non-transitory computer-readable storage media including RAM, ROM, EEPROM, CD-ROM or other optical disk storage, magnetic disk storage or other magnetic storage devices, flash memory devices (e.g., solid state memory devices), or any other storage medium which may be used to carry or store desired program code in the form of computer-executable instructions or data structures and which may be accessed by a general-purpose or special-purpose computer. Combinations of the above may also be included within the scope of computer-readable storage media. Computer-executable instructions may include, for example, instructions and data configured to cause the processor 84 to perform a certain operation or group of operations.

In some embodiments, one or more clinician monitoring devices 87 may be connected to the computing system 82 via a network 94. In these and other embodiments, the network 94 may include a wired or wireless network, and may have any suitable configuration, such as a star configuration, a token ring configuration, or other configurations. Furthermore, in some embodiments, the network 94 may include an Ethernet network, a local area network (LAN), a wide area network (WAN) (e.g., the Internet), and/or other interconnected data paths across which multiple devices may communicate. In some embodiments, the network 94 may include a peer-to-peer network. In some embodiments, the network 94 may also be coupled to or include portions of a telecommunications network that may enable communication of data in a variety of different communication protocols. In some embodiments, the clinician monitoring devices 87 may include or correspond to the clinician monitoring device 76 described with respect to FIG. 4.

In some embodiments, the network 94 may include BLUETOOTH® communication networks and/or cellular communications networks for sending and receiving data including via short messaging service (SMS), multimedia messaging service (MMS), hypertext transfer protocol (HTTP), direct data connection, wireless application protocol (WAP), e-mail, etc. The network 94 may enable communication via a standard-based protocol such as smart energy profile (SEP), Echonet Lite, OpenADR, or another suitable protocol (e.g., wireless fidelity (Wi-Fi), ZigBee, HomePlug Green, etc.).

In some embodiments, the communication unit 58 may be configured to transmit data to and receive data from the clinician monitoring devices 87 via the network 94. In some embodiments, the communication unit 58 may also be configured to transmit and receive data from a display screen and/or an electronic health record 100. In some embodiments, the display screen may include or correspond to the display screen 78 described with respect to FIG. 4. In some embodiments, the occlusion module 92 may be configured to send and receive data via the communication unit 58.

In some embodiments, the communication unit 58 may include a port for direct physical connection to the network 94 and/or another communication channel. For example, the communication unit 58 may include a universal serial bus (USB) port, a secure digital (SD) port, a category 5 cable (CAT-5) port, or similar port for wired communication with another device. In some embodiments, the communication unit 58 may include a wireless transceiver for exchanging data with the clinician monitoring device 87 or other communication channels using one or more wireless communication methods, including IEEE 802.11, IEEE 802.16, BLUETOOTH®, or another suitable wireless communication method.

In some embodiments, the communication unit 58 may include a cellular communications transceiver for sending and receiving data over a cellular communications network including via SMS, MMS, HTTP, direct data connection, WAP, e-mail, or another suitable type of electronic communication. The communication unit 58 may also provide other conventional connections to the network 94 for distribution of files or media objects using standard network protocols including transmission control protocol/internet protocol (TCP/IP), HTTP, HTTP secure (HTTPS), and simple mail transfer protocol (SMTP).

In some embodiments, an example of how the occlusion module 92 may manage flow conditions in a catheter assembly is now provided. In some embodiments, the occlusion module 92 may determine presence of an occlusion within the catheter assembly based on the data sensed by sensors, such as, for example, the sensors of the monitoring device 12 described with respect to one or more of FIGS. 1A-3D. In some embodiments, the occlusion module 92 may be configured to transmit the output signal from the communications module to the receipt location in response to determining the presence of the occlusion within the catheter assembly.

In some embodiments, the occlusion module 92 may be configured to determine the occlusion is partial in response to the sensors detecting a mean maximum pressure between 14 psi and 42.5 psi within a fluid pathway proximate the sensors. In some embodiments, the occlusion module 92 may be configured to generate an alert and/or output signal in response to determining the occlusion is partial. In some embodiments, the occlusion module 92 may be configured to determine the occlusion is full in response to the sensors detecting a mean maximum pressure of at least 42.5 psi. In some embodiments, the occlusion module 92 may be configured to generate the alert and/or the output signal in response to determining the occlusion is full.

In some embodiments, the occlusion module 92 may be configured to determine a pressure, such as the mean maximum pressure, within the catheter assembly is greater than a threshold value. In some embodiments, the occlusion module 92 may be configured to determine a fluid flow direction within the catheter assembly based on the data sensed by the sensors.

In some embodiments, an external server may include one or more components of the computing system 82. In some embodiments, the external server may be connected to the monitoring device 12 and/or the clinician monitoring device 87 via the network 94 or another network. Modifications, additions, or omissions may be made to the computing system 82 without departing from the scope of the present disclosure.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions may be described in detail, it should be understood that the various changes, substitutions, and alterations could be made hereto without departing from the spirit and scope of the invention.

The invention claimed is:

1. A monitoring device for detecting when a catheter is partially occluded, comprising:
  a first housing comprising a planar top surface, a distal end, a proximal end, a wall forming a tunnel extending through the proximal end and the distal end, and a fluid pathway extending through the tunnel, wherein the wall comprises a first hole and a second hole extending therethrough, wherein the distal end comprises a connector configured to couple to a catheter assembly, the first housing further comprising:
    a plurality of sensors disposed and spaced apart within the fluid pathway, wherein the plurality of sensors comprises a first sensor disposed within the first hole and a second sensor disposed within the second hole, wherein the first sensor and the second sensor enclose the fluid pathway within the tunnel between the distal end and the proximal end of the first housing;
    a first set of electrical contacts that connect to the plurality of sensors and are embedded in the planar top surface; and
    a groove in the planar top surface that extends from a first side of the first housing towards a second side of the first housing opposite the first side of the first housing; and
  a second housing having a planar bottom surface, the second housing comprising:
    a computing system having a processor that is configured to receive data sensed by the plurality of sensors, the processor being configured to detect, from the received data, when the catheter is partially occluded but not yet fully occluded, the computing system further comprising a communication unit by which the processor wirelessly transmits an output signal to a receipt location when the processor detects that the catheter is partially occluded;
    a second set of electrical contacts that connect to the computing system, the second set of electrical contacts being embedded in the planar bottom surface; and
    a protrusion that extends downwardly from the planar bottom surface, the protrusion extending from a first side of the second housing towards a second side of the second housing opposite the first side of the second housing, the protrusion being configured to slide into the groove in the planar top surface of the first housing to thereby secure the first housing to the second housing, wherein the protrusion and the groove are configured such that, when the protrusion is fully slid into the groove, the planar bottom surface is secured against and aligned with the planar top surface and the second set of electrical contacts align with and contact the first set of electrical contacts.

2. The monitoring device of claim 1, wherein the processor detects that the catheter is partially occluded by detecting that the received data defines a mean maximum pressure between 14 psi and 42.5 psi.

3. The monitoring device of claim 2, wherein the second housing comprises an indicator configured to provide an alert in response to the processor determining that the catheter is partially occluded.

4. The monitoring device of claim 3, wherein the second housing comprises another indicator configured to provide an alert in response to the processor determining that the catheter is fully occluded.

5. The monitoring device of claim 1, wherein the plurality of sensors comprises one or more pressure sensors configured to detect a fluid pressure of fluid within the fluid pathway.

6. The monitoring device of claim 5, wherein the plurality of sensors comprises one or more flow sensors configured to detect a fluid flow rate of the fluid within the fluid pathway.

7. The monitoring device of claim 5, wherein the plurality of sensors comprises two pressure sensors.

8. The monitoring device of claim 1, wherein the proximal end of the first housing comprises a luer connector.

9. The monitoring device of claim 1, wherein the processor is configured to wirelessly transmit another output signal to the receipt location in response to detecting when the catheter is fully occluded.

10. The monitoring device of claim 9, wherein the plurality of sensors comprises two pressure sensors, wherein the processor detects that the catheter is partially occluded by detecting that the received data defines a mean maximum pressure between 14 psi and 42.5 psi.

11. The monitoring device of claim 10, wherein the processor detects that the catheter is fully occluded by detecting that the received data defines a mean maximum pressure greater than 42.5 psi.

12. The monitoring device of claim 1, wherein the processor detects that the catheter is partially occluded by detecting that the received data defines a mean maximum pressure between two threshold values.

13. The monitoring device of claim 1, wherein the plurality of sensors comprises two pressure sensors, wherein the processor is configured to determine, based on the data sensed by the plurality of sensors, a fluid flow direction within the catheter assembly.

14. The monitoring device of claim 1, wherein the protrusion has an inverted T-shape and the groove has a corresponding inverted T-shape, wherein the protrusion and the groove are configured such that, when the inverted T-shape is fully slid into the corresponding inverted T-shape the planar bottom surface is secured against and aligned with the planar top surface and the second set of electrical contacts align with and contact the first set of electrical contacts.

* * * * *